United States Patent [19]

Kolb et al.

[11] 4,237,733
[45] Dec. 9, 1980

[54] SAMPLING DEVICE FOR MEASURING INSTRUMENTS

[75] Inventors: Bruno Kolb, Owingen; Michael Jaklin, Bodman-Ludwigshafen; Peter Pospisil, Uberlingen; Dietrich Boege, Daisendorf; Hubertus Riegger, Uberlingen, all of Fed. Rep. of Germany

[73] Assignee: Bodenseewerke Perkin-Elmer & Co. GmbH, Uberlingen, Fed. Rep. of Germany

[21] Appl. No.: 67,069

[22] Filed: Aug. 15, 1979

Related U.S. Application Data

[63] Continuation of Ser. No. 32,620, Apr. 23, 1979, abandoned.

[30] Foreign Application Priority Data

Apr. 26, 1978 [DE] Fed. Rep. of Germany ....... 2818251

[51] Int. Cl.$^3$ ............................................. G01N 1/10
[52] U.S. Cl. ................................................. 73/423 A
[58] Field of Search .................... 73/422 GE, 423 A; 422/64, 65, 68; 141/130

[56] References Cited

U.S. PATENT DOCUMENTS

| | | |
|---|---|---|
| 3,545,279 | 12/1970 | Jentzsen . |
| 3,549,330 | 12/1970 | Jungner ................................. 422/64 |
| 3,631,724 | 1/1972 | Oster ................................ 73/423 A |
| 3,764,268 | 10/1973 | Kosowsky ........................... 141/130 |

FOREIGN PATENT DOCUMENTS 1284660 6/1966 Fed. Rep. of Germany .
1297904 6/1969 Fed. Rep. of Germany .

Primary Examiner—S. Clement Swisher
Attorney, Agent, or Firm—Salvatore A. Giarratana; Francis L. Masselle; Edwin T. Grimes

[57] ABSTRACT

The sample device includes a magazine having a rotatable turntable carrying a plurality of circumferentially spaced chambers for receiving sample vessels and movable axially between a sample changing positon and a sampling position. In the sample change position, each sample vessel is pushed against a laterally displaceable closure plate to uncover an aperture in a bottom closure member whereby the sample vessel is receivable in a chamber registered with the aperture. A cradle is carried by the bottom closure member to support the sample vessel as it is displaced through the aperture into the registering chamber. When a selected vessel is aligned with a sampling opening through a closure plate on the opposite side of the turntable, the magazine is displaced axially into the sampling position with the axial displacement causing a needle to pierce the self-sealing diaphragm on the sample vessel. Sampling is effected by pressurizing the vessel and drawing sample components in the vapor phase into the injection block of the gas chromatographic instrument.

27 Claims, 6 Drawing Figures

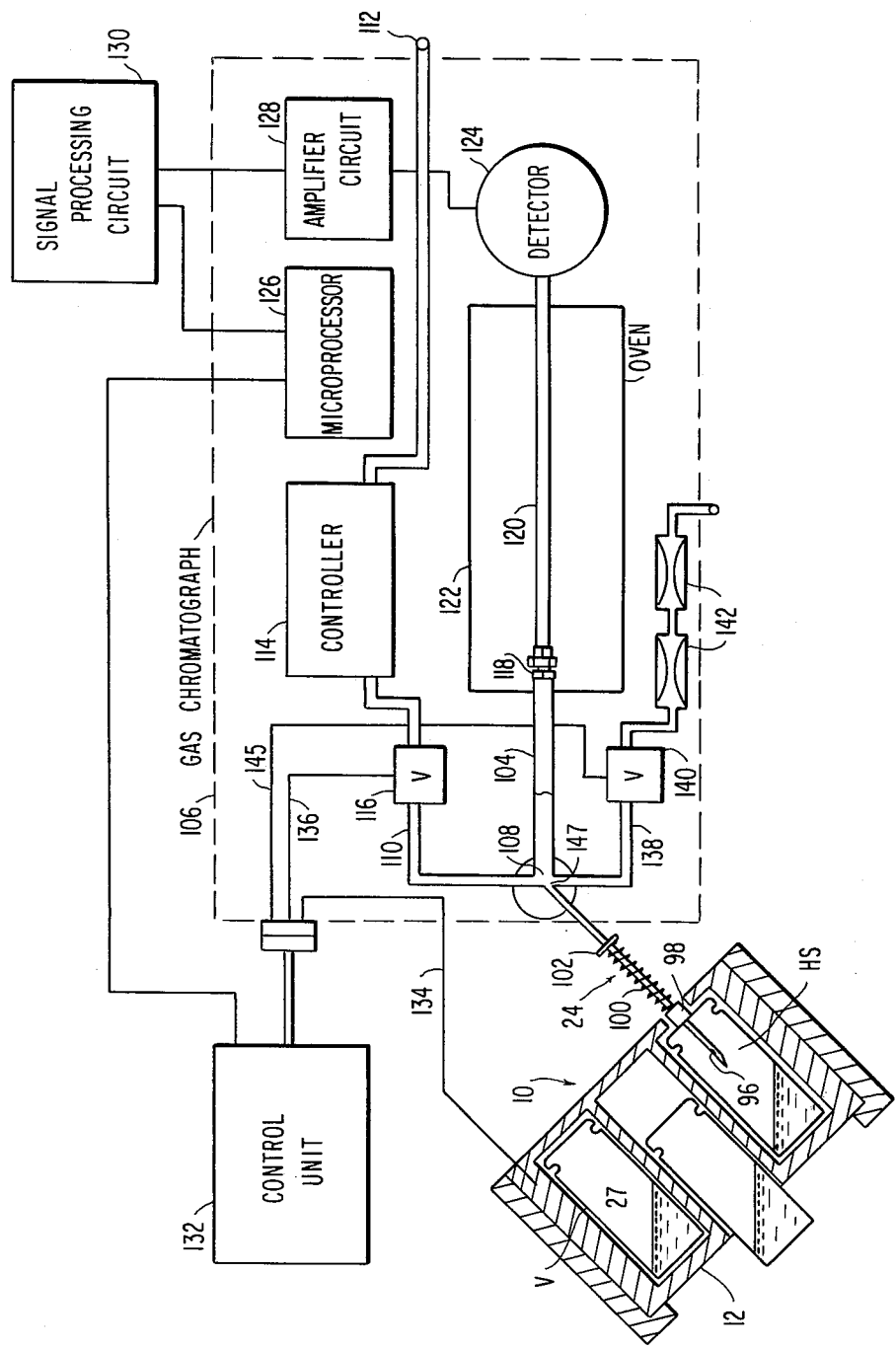

SAMPLING DEVICE FOR MEASURING INSTRUMENTS

BACKGROUND OF THE INVENTION

This application is a continuation of Application Ser. No. 32,620 filed Apr. 23, 1979 now abandoned.

The present invention relates to a sampling device for measuring instruments and particularly relates to a semi-automatic sampling device for gas chromatographic vapor space analysis.

Gas chromatographic vapor space analysis (head space) is particularly suitable for the determination of volatile components in samples of heterogeneous composition where usual syringe injection cannot be employed. The samples may include solid materials or highly viscous liquids. This head space technique is also particularly suitable for the analysis of liquids containing a high proportion of non-volatiles. Only the volatile components of interest are analyzed, while the non volatile residue of the sample does not effect the sample of the analysis.

In utilizing the head space method, a sample is enclosed in a sample vessel by means of a self-sealing diaphragm. A state of equilibrium of the volatile components between the sample and the vapor space above the sample is established in the sample vessel closed by the diaphragm whereby the various sample components are contained within the head space above the sample. In this state of equilibrium, a sample component which is contained in high concentration in the sample will also have high partial pressure in the head space.

In sampling devices for chormatographic instruments utilizing the head space method, vapor from the head space is supplied to the gas chromatographic by a sampling device. In order to provide repeated and accurate measurements, the sample must be maintained at a well defined substantially high temperature. In German Pat. No. 1,297,904, there is disclosed a sampling device for gas chromatographs wherein a turntable accomodating the sample vessels comprises a thermostatized liquid bath. The turntable is mounted for vertical movement and is moved upwardly to push a sample vessel onto a hollow needle such that the hollow needle pierces the diaphragm closing the sample vessel. The needle is connected to the inlet of a heated injection block which communicates with a carrier gas conduit through a valve. Carrier gas flowing through the carrier gas conduit flows through the needle after the needle has pierced the diaphragm and into the sample vessel, whereby a total pressure equal to the carrier gas pressure at the inlet of the injection block is obtained in the interior of the sample vessel. For feeding the sample, the valve in the carrier gas conduit is closed for a predetermined time period. Pressure compensation occurs and the higher pressure prevailing within the sample vessel causes the gas mixture to flow into the injection block. Subsequently, the turntable with the thermostatized liquid bath is lowered and the valve is opened, whereby the carrier gas flows again through the injection block and the separating column to convey the sample through the separating column.

In German published Pat. Specification No. 1,284,660, the needle is disposed in a plunger sealingly movable within a cylinder having a restricted outlet. The cylinder is provided with a self-sealing diaphragm at its lower end face. A spring is provided between the cylinder and plunger to normally maintain the plunger in a position relative to the cylinder such that the tip of the needle is located within the cylinder. Thus, carrier gas supplied to the cylinder vents to the atmosphere as a quantitatively small stream through the restricted outlet of the cylinder. When sample is to be fed, the sample vessel with its self-sealing diaphragm is urged upwardly against the cylinder to displace the cylinder upwardly against the bias of the spring. This causes the needle to pierce the diaphragm closing the end face of the cylinder and subsequently pierce the diaphragm of the sample vessel.

SUMMARY OF THE PRESENT INVENTION

Accordingly, it is a primary object of the present invention to provide a novel and improved sampling device for gas chromatographic vapor space analysis which is simple in construction, reliable and semi-automated in operation.

It is another object of the present invention to provide a novel and improved sampling device for gas chromatographic vapor space analysis which facilitates the insertion of sample vessels into the sampling device and their removal therefrom.

It is still another object of the present invention to provide a novel and improved sampling device for gas chromatographic vapor space analysis wherein the critical phases of the sampling cycle are precisely controlled resulting in a substantially constant injected head space gas volume.

It is a further object of the present invention to provide a novel and improved sampling device for gas chromatographic vapor space analyses having the foregoing characteristics and wherein temperature and pressure conditions remain substantially constant from sample to sample with precise theromostating over a substantial range.

Additional objects and advantages of the invention will be set forth in part in the description which follows and in part will be obvious from the description, or may be learned by practice of the invention. The objects and advantages of the invention may be realized and attained by the means of the instrumentalities and combinations particularly pointed out in the appended claims.

To achieve the foregoing objects and in accordance with the purpose of the present invention, as embodied and broadly described herein, a sampling device constructed in accordance with the present invention and having a conduit for transporting samples from sample vessels to a gas chromatographic instrument comprises a support, a turntable carried by the support for rotation about an axis and having a plurality of chambers spaced one from the other about said axis for receiving sample vessels, said chambers opening axially through axially opposite end faces of the turntable, means carried by the turntable for heating the sample vessels disposable in the chambers, means in opposition to one end face of the turntable for closing the chamber openings through the one end face and including an aperture for selective registration with the chamber openings upon relative rotation of the turntable and the closing means whereby a sample vessel is disposable through the aperture and registered chamber opening for reception in the corresponding chamber, and means for mounting the turntable for movement in an axial direction between a first rest position and a second position enabling insertion of the conduit through a selected chamber opening in the opposite end face and into the corresponding chamber to draw sample from a sample vessel in the corresponding chamber.

Preferably, the turntable comprises a metal block. The heating means includes an electrical heater coil disposed about the block. A closure member is mounted for rotation about the axis of rotation of the turntable and includes a surface inclined to the axis to enable the closure member to be moved laterally to open the aperture upon movement of a sample vessel against the inclined surface and toward the chamber registered with the aperture. Also, means are provided for indexing the turntable into pre-selected positions with the chambers in selected registry with an opening in a cover plate overlying the opposite end face of the turntable and to register the opening of another chamber at the one end face of the turntable with the aperture by which an additional sample vessel may be inserted into the magazine.

The invention consists in the novel parts, constructions, arangements, combinations and improvements shown and described. The accompanying drawings, which are incorporated in and constitute a part of the specifications, illustrate one embodiment of the invention, and, together with the description, serve to explain the principles of the invention.

DESCRIPTION OF THE DRAWING FIGURES

FIG. 6 is a schematic illustration showing the arrangement of the sampling device hereof in combination with a gas chromatograph and the flow circuits therefor.

DESCRIPTION OF A PREFERRED EMBODIMENT

Reference will now be made in detail to the present preferred embodiment of the invention, an example of which is illustrated in the accompanying drawings.

Figure 3:
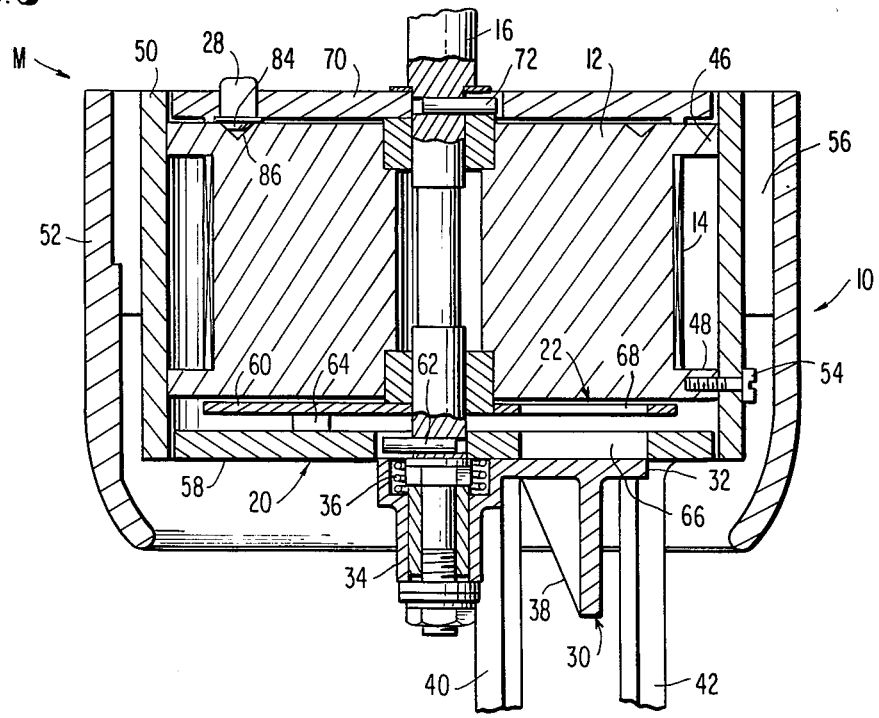
FIG. 3 is a vertical cross-sectional view taken generally about on line 3—3 in FIG. 1.

Referring now to the drawings, there is illustrated a sampling apparatus constructed in accordance with the present invention and including a magazine generally indicated M, having a turntable 10 comprising a block 12, preferably formed of metal, heated by an electrical heater coil 14 (FIG. 3), wrapped circumferentially thereabout. Metal block 12 is mounted for rotation about the axis of a non-rotatable shaft 16 carried by a bushing 88 (FIG. 5) mounted on a support 82. Shaft 16, however, is guided for movement in an axial direction, for example by a spline in bushing 88. Metal block 12 includes a plurality of bores or chambers 18 which open through the opposite end faces of turntable 10. Chambers 18 are disposed about shaft 16 and are preferably arranged in a circular array or pattern about shaft 16. A cover plate, generally indicated 20 in FIG. 3, is supported by stationary shaft 16 and underlies bores 18. Cover plate 20 has an aperture, generally indicated 22 in FIG. 3, utilized to shift a sample vessel V (FIG. 6) into the respective bore of chamber 18 aligned with aperture 22. A hollow needle (FIG. 6), generally designated 24, is provided for insertion into a sample vessel V in a selected chamber 18 when shaft 16 is displaced in a upwardly direction as illustrated in FIG. 6.

It will also be appreciated from FIG. 6 that shaft 16 extends at an acute angle with respect to the vertical whereby metal block 12 is also inclined to the vertical. This inclination increases the surface area 27 (FIG. 6) of the sample liquid thus enhancing the ensuing equilibrium between the sample liquid in vessel V and the head space HS above the sample liquid.

Metal block 12 is also arranged to be arrested in a selected one of a plurality of rotatable or angular positions about shaft 16 by a detent, generally indicated 28 in FIG. 3. In each detented position, a selected chamber 18 is aligned with the aperture 22 in cover plate 20 and another selected chamber 18 is aligned with hollow needle 24.

A cover member, generally indicated 30 (FIG. 3), underlies aperture 22 and includes a closure plate 32 mounted on and for rotation about shaft 16 by a hub 34. Closure plate 32 is held in a position closing aperture 22 by a spring 36, preferably a helical spring, which surrounds shaft 16. One end of spring 36 is suitably secured to shaft 16 and its opposite end is secured to closure plate 32. Cover member 30 also has an inclined surface 38 depending from closure plate 32 on the side thereof remote from turntable 10. Closure plate 32 is thus mounted for displacement in a lateral direction relative to the axis of shaft 16 in response to engagement of a sample vessel against inclined surface 38 and movement of the sample vessel in an axial direction toward turntable 10.

Figure 5:
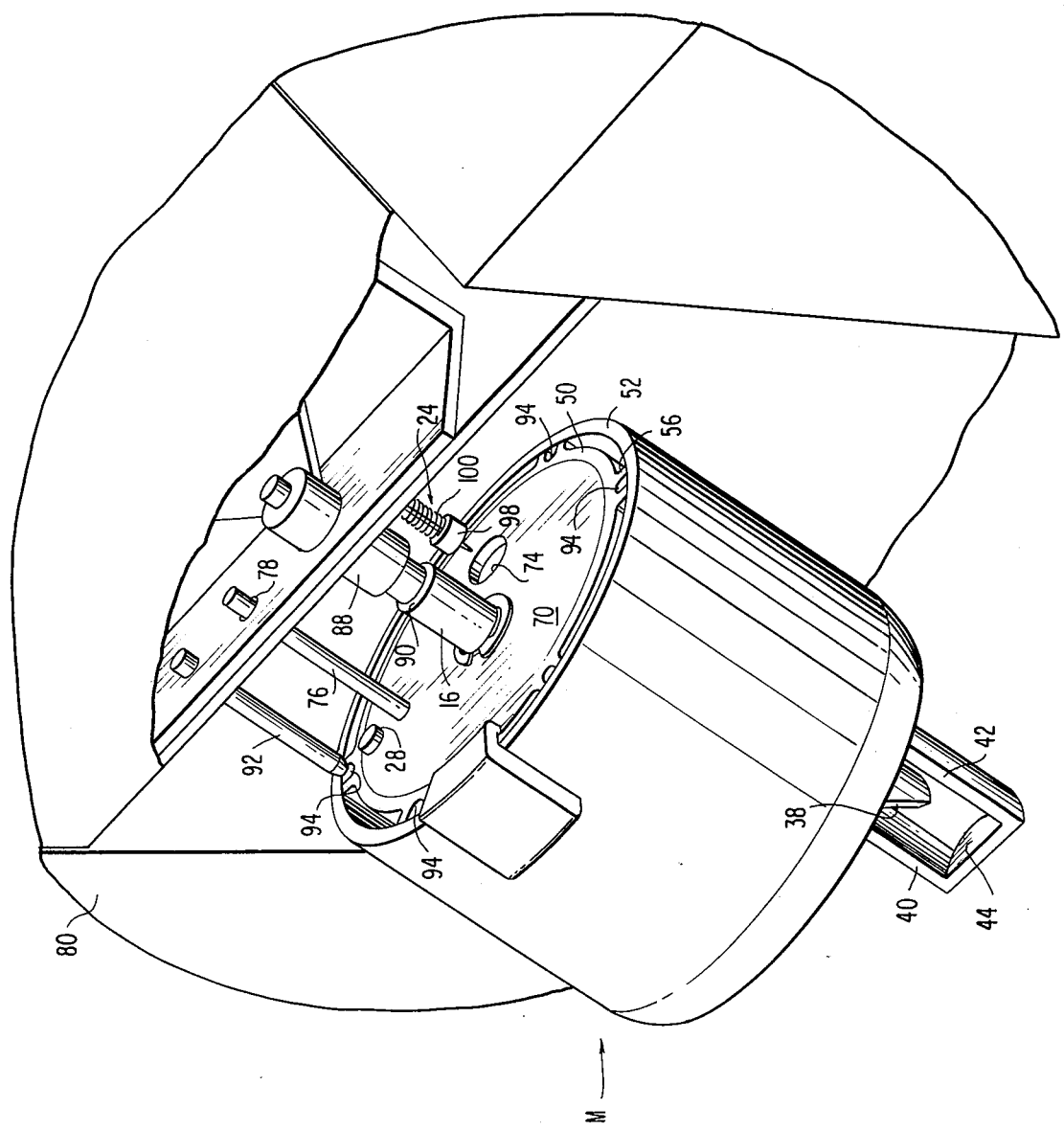
FIG. 5 is a perspective view of a sampling device constructed in accordance with the present invention and illustrated installed in a gas chromatograph.

A cradle is provided for facilitating insertion of sample vessels V into magazine M and includes parallel guide rods 40 and 42 which project in an axial direction away from the lower surface of cover plate 20. Rods 40 and 42 straddle or lie on both sides of aperture 22 and are arcuately shaped in cross section. As illustrated in FIG. 5, the lower ends of guide rods 40 and 42 are interconnected by a support 44, preferably a semi-circular disc, which also forms part of the cradle. A sample vessel V is thus disposable in the cradle and between guide rods 40 and 42 and against support disc 44 preparatory to its insertion into magazine M. Manual movement of the sample vessel V along the cradle by means of a push rod, not shown, and in an axial direction toward turntable 10 causes the vessel V to engage inclined surface 38 and push closure plate 32 aside whereby the vessel V may be inserted into the chamber 18 in axial registration with aperture 22. After insertion, closure plate 32 returns under the action of spring 36 into its original position covering aperture 22. This action is repeated for each vessel desired to be located into the magazine.

Metal block 12 is generally cylindrical and has projections 46 and 48 which project radially at circumferentially spaced locations about block 12 at its top and bottom. As noted previously, heater 14 is an electrical heater coil and is wrapped about the peripheral surface of metal block 12 between radial projections 46 and 48. Metal block 12 is also surrounded by inner and outer sleeves or cylindrical jackets 50 and 52, respectively. Inner jacket 50 is secured to radial projections 46 and 48, preferably by screws 54. Outer jacket 52 is spaced from and coaxially with inner jacket 50 and is maintained in this arrangement by radial ribs 56. Thus, the two jackets and the annular air gaps formed therebetween and between the inner jacket 50 and metal block 12 provide heat insulation such that turntable 10 can be manually handled at its outer jacket and rotated manually. If desired, outer jacket 50 can be corrugated in external shape.

Figure 1:
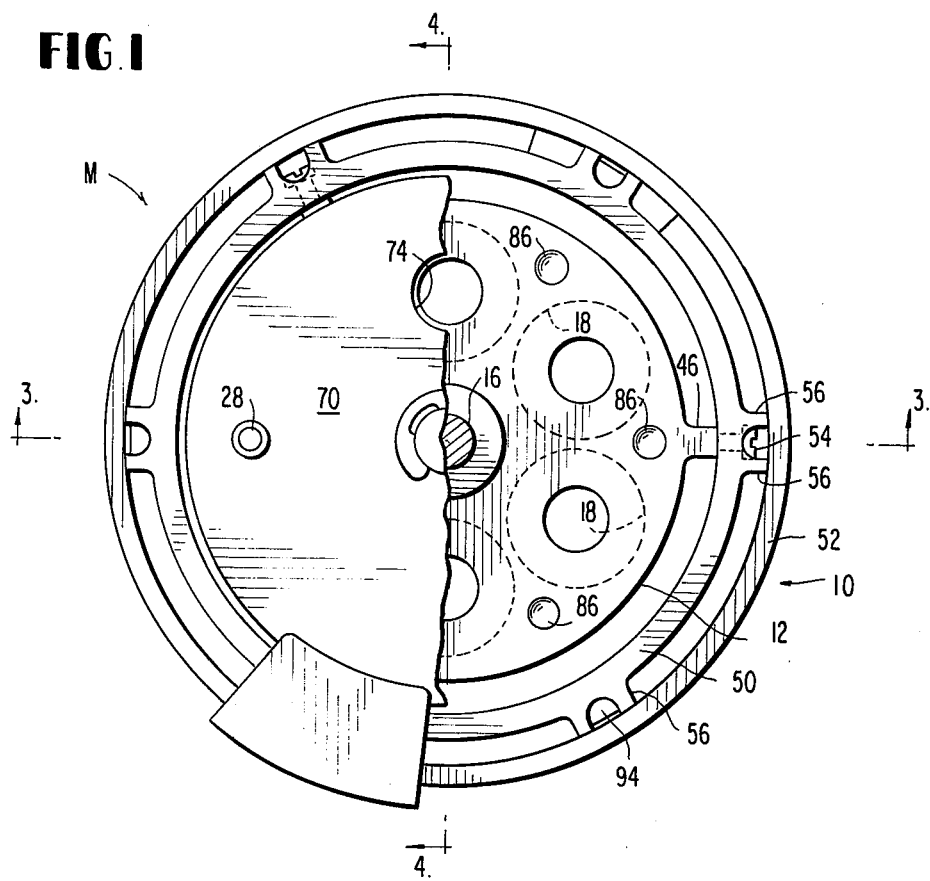
FIG. 1 is a plan view of a magazine forming a part of the sampling device of the present invention with the right half of the upper end plate of the magazine removed to expose the upper end face of the turntable.
Figure 2:
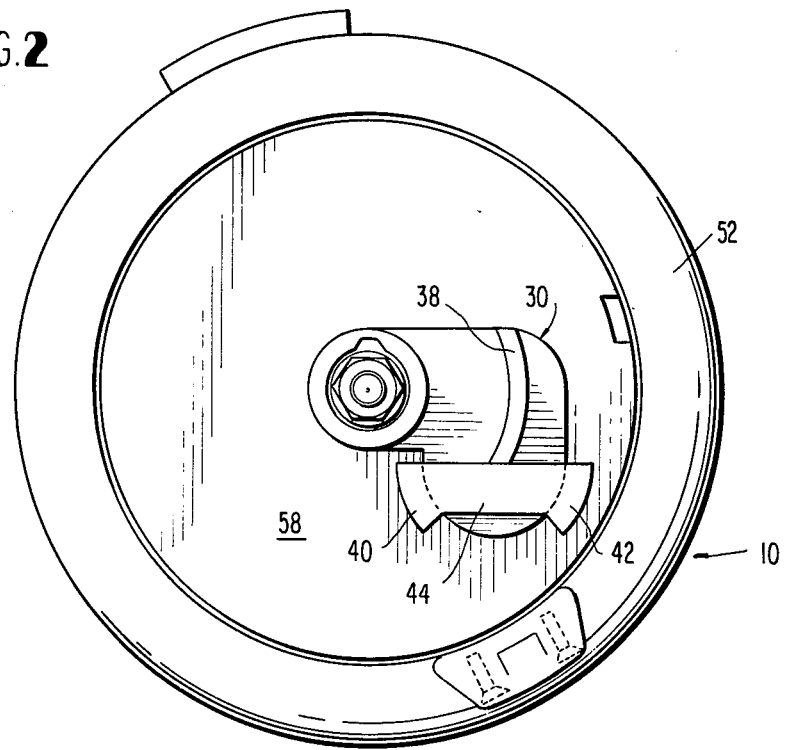
FIG. 2 is a bottom plan view of the magazine illustrated in FIG. 1.
Figure 4:
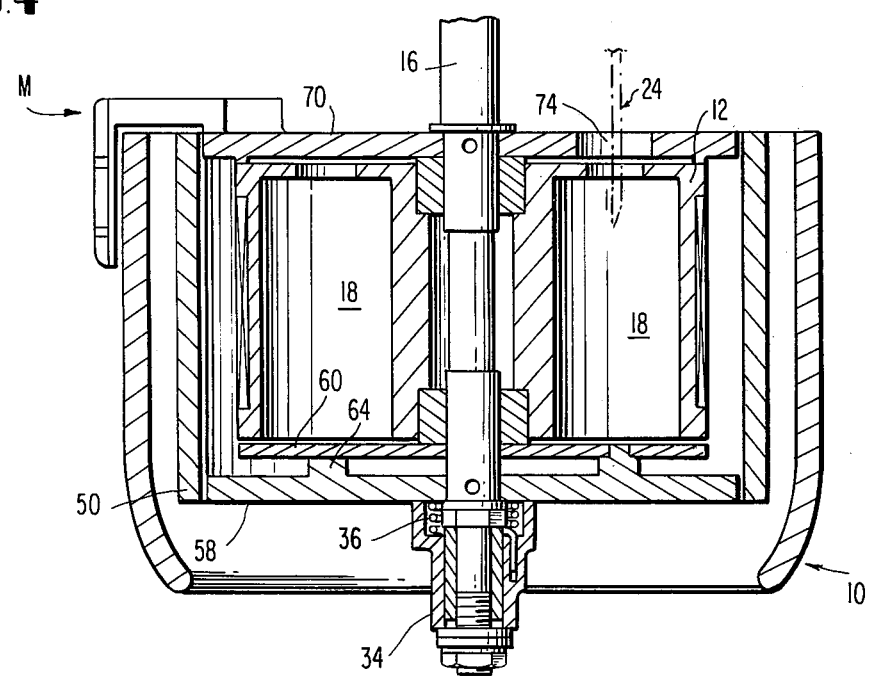
FIG. 4 is a view similar to FIG. 3 taken generally about one line 4—4 in FIG. 1.

Cover plate 20 also includes lower and upper parallel plate members 58 and 60 respectively. Lower plate member 58 is non-rotatably connected to shaft 16 by a transverse pin 62. Upper plate member 60 is spaced from lower plate member 58 by spacer 64 (FIG. 3). Aligned apertures 66 and 68 are provided in both plate members 58 and 60 and form aperture 22. An upper end plate 70 is also non-rotatably connected to shaft 16 opposite the other or upper end face of metal block 12 by a transverse pin 72. Upper end plate 70 has an aperture 74 (FIGS. 1 and 4) for receiving hollow needle 24. A pin 76 (FIG. 5) is suitably secured to and at a location off the axis of upper end plate 70 and extends through an aperture 78 in a base plate 82 affixed to the instrument frame 80. Detent 28 includes a spring biased pin 84 carried by and projecting from frame 70. Pin 84 cooperates with circumferentially spaced recesses 86 formed on the upper end face of metal block 12 to detent turntable 10 in selected rotational positions about the axis of shaft 16. As will be appreciated from the ensuing description, detent 84 determines the operative positions of turntable 10 with respect to locating chambers 18 in registration with apertures 74 and 22 adjacent opposite end faces of turntable 10.

Shaft 16 is mounted on instrument frame 80 in a bearing bushing 88 (FIG. 5) for axial displacement between a lower position, in which turntable 10 is rotated to change the sample vessels V, and an upper position, in which hollow needle 24 penetrates a selected sample vessel V. A shoulder 90 on shaft 16 engages the end face of bearing bushing 88 to provide a stop for turntable 10 when in its upper position.

An interlocking means cooperates with block 12 and permits movement of block 12 toward hollow needle 24 only when a selected chamber 18 is axial aligned with needle 24. The interlocking means, in addition, prevents rotary movement of block 12 when in its upper position. To this end, the interlocking means includes a stationary interlocking pin 92 (FIG. 5) which is attached to the instrument frame 88 in parallel relation to shaft 16. The lower end of pin 92 is disposed in opposition to inner jacket 50 when block 12 is in its lower position. When needle 24 is aligned with one of the chambers 18, interlocking pin 92 will be aligned with a respective axial recess 94 (FIGS. 1 and 5) of inner jacket 50. Alternately, pin 92 may be aligned with suitable apertures, not shown, in upper end plate 70 and block 12. In this manner, block 12 cannot be displaced upwardly with shaft 16 when needle 24 is not aligned with a chamber 18 through opening 74 because the end face of inner jacket 50 or cover 70 would otherwise engage the lower end of pin 92. Furthermore, block 12 is prevented from rotation when in its upper position by reception of the interlocking pin 92 in the selected axial recess 94. This avoids damaging needle 24 when received in the corresponding chamber 18.

As illustrated in FIG. 6, needle 24 has a lateral inlet and outlet opening 96 adjacent its sharpened tip. A rubber plug 98 is guided on needle 24 and, in its inoperative position, is held, under the action of a helical spring 100, in a position closing inlet and outlet opening 96. Helical spring 100 is backed at its upper end by an abutment 102.

In the inoperative position, when turntable 10 is retracted to the left and lies in its lower sample vessel changing position as illustrated in FIG. 6 and with needle 24 retracted from the sample vessel V and the opening 74 of turntable 10, the inlet and outlet opening 96 of needle 24 is closed by rubber plug 98. In this position, carrier gas cannot flow from needle 24. Upon axial movement of turntable 10 into its upper sampling position and consequent penetration of needle 24 into a sample vessel V, rubber plug 98 engages the self-sealing diaphragm of the sample vessel V in registration with needle 24 and is pushed back against the action of helical spring 100 to expose inlet and outlet opening 96 within the head space HS of vessel V. As illustrated in FIG. 6, needle 24 is in direct heat conducting contact with a heated injection block 104 of gas chromatograph 106. Thus, needle 24 is heated by heat conduction from injection block 104 eliminating the need for a separate heater for needle 24.

The arrangement of the sampling device of the present invention in combination with a gas chromatograph 106 is illustrated in FIG. 6. Gas chromatograph 106 includes injection block 104 which has an inlet 108 connected to a carrier gas conduit 110. Carrier gas conduit 110 communicates with a carrier gas port 112 through a controller 114 and a solenoid valve 116. Controller 114 may be a pressure regulator or a flow controller.

An outlet 118 of injection block 104 is connected to a separating column 120 disposed within an oven 122. A detector 124 is located at the outlet of column 120. The operation of the gas chromatograph is controlled by a microprocessor 126. A signal from detector 124 is amplified in a suitable amplifier circuit 128 and supplied to a signal processing circuit 130 which also receives a signal from microprocessor 126. In addition, microprocessor 126 provides a signal to control unit 132 for controlling the sampling apparatus. Control unit 132 controls the power to the electric heater coil 114, as indicated by conductor 134. In addition, unit 132 controls the actuation of valve 116 in the carrier gas conduit 110 through a conductor 136.

As illustrated, needle 24 opens into an outlet passage 138 which contains a solenoid actuated control valve 140 and a restrictor 142. Valve 140 is actuated by means of an electrical lead 145 connected to control unit 132. Outlet passage 138 communicates with inlet 108 of injection block 104, the inner end 147 of needle 24 being located closely downstream of injection block 104 and upstream of control valve 140.

The sampling apparatus described and illustrated is utilized by first inserting the sample vessels V into the heated magazine utilizing the cradle in the manner previously described. The turntable, of course, lies in the lower sample changing position to effect this loading. After the sample vessels are in the magazine, the sample compounds are vaporized and equilibration between the sample materials and the generated vapor phase takes place. The turntable is then manually rotated to locate the proper sample vessel V in proper rotary sampling or inject position, i.e. in axial registration with the needle 24 through opening 74. The magazine is then manually displaced axially toward needle 24 from its sample changing position into its upper or elevated sampling position and against the axial stop 90. In displacing the turntable into the sampling position, the needle 24 penetrates the self sealing diaphragm on the sample vessel and enters the head space HS above the sample within the sample vessel. Valve 116 is then opened and the preheated carrier gas is supplied through needle 24 to the vessel V. Valve 140 is, of course, closed. The pressurization of the vessel continues and the gas pressure in the vessel V equalizes with the column headpressure. During pressurization, however, carrier gas continues to flow through column 120. After a predetermined time necessary to thoroughly mix the carrier gas and the sample vapor in the head space HS, valve 116 is closed. Closing valve 116 ends the pressurization period and, because pressure compensation occurs, sample flows from the head space HS through needle 24 into the injection block 104. This injection occurs over a predetermined time period after which valve 116 is once again opened to terminate the sample feeding from the sample vessel V. Valve 140 is also opened. This enables the carrier gas stream to convey the sample from the injection block 104 through column 120 for analysis.

When a pressure controller is used as controller 114, and needle 24 remains in sample vessel V during the analysis, vapor from the head space of sample vessel V could diffuse through needle 24 into the carrier gas stream and disturb the analysis. To prevent this, needle 24 does not communicate directly into inlet 108 of injection block 104. Rather, it communicates with outlet passage 138 slightly downstream of inlet 108. With valves 116 and 140 open, a small carrier gas stream will flow continuously through outlet passage 138 and will carry away any sample vapors which have diffused through needle 124. This carrier gas stream thus flows in opposition to the sample vapors on their way to inlet 108 of injection block 104. During sample feeding, valve 140 is, of course, closed under the control of control unit 132 by way of conductor 145. Thus readily reproducible injected gas volumes and consequent reproducible quantitative test results are ensured.

If a flow controller is used as controller 114 to control the flow rate of the carrier gas in conduit 110 in lieu of a pressure controller and during carrier gas injection into sample vessel V, the pressure build-up in sample vessel V is a function of the time constant of the flow controller and the impedance of the column. In this case, it is advantageous to open valve 116 in the carrier gas conduit by a time control switch actuated in response to displacement of block 12 into its upper position. Thus, after block 12 has been displaced axially into the sampling position, and for a predetermined time interval adapted to the time constant of flow controller 114, valve 116 is opened. This insures that sample feeding by closing valve 116 is effected only after sufficient pressure has built up within the sample vessel. With this mode of operation, the turntable 10 is returned to its sample changing position as illustrated in FIG. 6 so that inlet and outlet opening 96 of needle 24 is closed by rubber plug 98.

To unload the magazine, the turntable is rotated to align the chamber 18 containing the sample to be unloaded with aperture 22. By pushing the cover member 30 to one side against the bias of spring 36 and exposing aperture 22, the used sample vessel will slide out onto the cradle for removal.

It will be apparent to those skilled in the art that various modifications and variations can be made in the sampling device of the present invention without departing from the scope or spirit of the invention.

What we claim is:

1. A sampling device having a conduit for transporting samples from sample vessels to the column of a gas chromatograph comprising:
   a magazine for use with the gas chromatograph,
   a turntable carried by said magazine for rotation about an axis and having a plurality of chambers spaced one from the other about said axis for receiving sample vessels, said chambers opening axially through axially opposite end faces of said turntable,
   means for heating the sample vessels received in said chambers;
   means in opposition to one end face of said turntable for closing the chamber openings through said one end face and including an aperture for registration with selected chamber openings upon relative rotation of said turntable and said closing means whereby a sample vessel is disposable through said aperture for reception in a selected chamber in registry with said aperture, and,
   means mounting said magazine for movement in an axial direction between a first rest position and a second position enabling insertion of the conduit through a selected chamber opening in the opposite end face of said turntable and into the corresponding chamber for withdrawing sample from a sample vessel in the corresponding chamber.

2. A sampling device according to claim 1 wherein said turntable comprises a metal block, said heating means including an electrical heater coil disposed about said block, said chamber openings being disposed in a circular array about said axis, said mounting means including a shaft having an axis coincident with said rotational axis, and means coupling said turntable and said shaft one to the other for conjoint axial movement.

3. A sampling device according to claim 1 wherein said axis extends at an acute angle to the vertical whereby the sample vessels in said chamber are inclined to the vertical.

4. Apparatus according to claim 1 including means for releasably detenting said turntable in selected rotary positions corresponding to the rotary positions in which the respective chamber openings register with said aperture.

5. A sampling device according to claim 1 including a closure member carried by said magazine for selectively closing said aperture and means mounting said closure member for movement between positions opening and closing said aperture.

6. Apparatus according to claim 5 wherein said mounting means includes a shaft having an axis coincident with said rotational axis, and means coupling said turntable and said shaft one to the other for conjoint axial movement, means for biasing said closure member into a position closing said aperture, said closure member including a surface inclined to said axis enabling said closure member to be moved toward its opening position upon movement of a sample vessel against said inclined surface and toward said turntable.

7. Apparatus according to claim 1 including a cradle carried by said closing means for guiding a sample vessel for movement through said aperture, said cradle projecting from said closing means on the side of said aperture remote from said turntable.

8. Apparatus according to claim 7 wherein said cradle includes a pair of generally parallel guide rods and a support member carried adjacent the remote ends of said rods for supporting a sample vessel prior to insertion of the sample vessel through said aperture.

9. Apparatus according to claim 1 including means carried by said magazine defining a plurality of predetermined rotary positions thereof for insertion of the conduit and into which positions said chambers are selectively rotated, and means for precluding axial movement of said magazine into said second position when said chambers lie in rotary positions other than said predetermined rotary positions.

10. Apparatus according to claim 1 including means carried by said magazine defining a plurality of predetermined rotary positions thereof for insertion of the conduit, said turntable being rotatable to locate respective chambers in said predetermined rotary positions and means enabling axial movement of said magazine into said second posiion only when said chambers respectively lie in said predetermined rotary position.

11. Apparatus according to claim 1 including means for preventing rotation of said turntable when said turntable lies in said second position.

12. In a sampling device for gas chromatographic instrument having a hollow needle for use as a capillary connection conduit for taking samples from sample vessels closed by self-sealing diaphragms, a separating column in communication with the hollow needle, a carrier gas conduit having a valve therein and leading to the inlet of the separating column, said valve being closed for the purpose of sampling feeding, and a turntable for receiving a plurality of sample vessels, the turntable being rotatable to locate each of the sample vessels below the stationary hollow needle, the improvement comprising; a heater carried by said turntable, said turntable comprising a metal block heated by said heater and serving as a thermostat, a shaft, said turntable being mounted for rotation about said shaft and having a circular array of through-bores located about the axis of said shaft extending in an axial direction, means for restraining said shaft from rotation and enabling movement thereof and said turntable in an axial direction, a cover plate carried by said shaft covering the axial through-bores along one side of said turntable and having an aperture enabling a sample vessel to be inserted into the respective through-bore aligned with said aperture, said shaft and said turntable be axially movable in a direction toward said needle to push a sample vessel about the hollow needle whereby the needle pierces the diaphragm.

13. A sample device according to claim 12 wherein said shaft extends at an acute angle with respect to the vertical.

14. A sampling device according to claim 12 including a detent for arresting said metal block in predetermined angular positions about said axis with one of said through-bores in each angular position in registery with said aperture in said cover plate and another through-bore in registry with said hollow needle.

15. A sampling device according to claim 14 including a laterally movable cover member, means mounting said cover member for lateral movement into positions offset from and in registration with said aperture.

16. A sampling device according to claim 15 wherein said cover member is rotatably mounted in said shaft, a spring for holding said cover member in position in registration with said aperture, said cover member having an inclined surface on its lower side remote from said cover plate, said cover member being movable laterally by pushing a sample vessel axially against said inclined surface.

17. A sampling device according to claim 16 including parallel guide rods projecting in an axial direction from the lower surface of said cover plate on opposite sides of said aperture, the sample vessels being receivable in an axial direction through said aperture and into the through-bore of said metal block between said guide rods.

18. A sampling device according to claim 17 including a support disc carried by the lower ends of said guide rods.

19. A sampling device according to claim 12 including an interlocking means cooperable with said turntable to enable displacement of said metal block toward the hollow needle only when one of said through-bores is aligned with said hollow needle and to prevent rotary movement of the turntable in its axially displaced position.

20. A sampling device according to claim 19 including a stationary interlocking pin for projection from the instrument frame, said block having a plurality of axial recesses, the lower end face of said pin being located in registration with one of said recesses when the hollow needle is aligned with one of the through-bores.

21. A sampling device according to claim 12 wherein said metal block is generally cylindrical and has radial projections adjacent its top and bottom, said heater including an electric heater coil disposed between said projections on the peripheral surface of said metal block, said block being surrounded by inner and outer jacket parts, said inner jacket part being attached to the radial projections, the outer jacket part being held spaced from and coaxial with said inner jacket part by radial ribs.

22. A sampling device according to claim 21 wherein said cover plate comprises a lower plate member and an upper plate member parallel thereto, said lower plate member being non-rotatably connected to said shaft, and spaced from said upper plate member, said upper and lower plate members having aligned apertures for receiving sample vessels.

23. A sampling device according to claim 22 including an upper end plate non-rotatably connected to said shaft above said block and having an aperture for receiving said needle, an axial pin attached off center to said upper end plate and extending through an aperture of a base plate fixed to the instrument when said turntable lies in its position axially displaced toward said needle, and a detent on said upper end plate, the end face of said metal block having recesses cooperable with said detent to detent said block in predetermined angular positions.

24. A sampling device according to claim 12 wherein said needle has a lateral inlet and outlet opening, a plug guided for axial movement on said hollow needle, and a helical spring for holding said plug in a position sealingly closing said inlet and outlet opening.

25. A sampling device according to claim 24 including a heated injection block, said needle being in direct heat conducting contact with said heated injection block and arranged to be heated solely by heat conduction from said injection block.

26. A sampling device according to claim 25 wherein the instrument includes an outlet passage having a control valve and a restrictor, said needle opening into said outlet passage, said outlet passage extending from the inlet of said injection block, a carrier gas conduit carried by said instrument and connected to the inlet of said injection block, the end of said needle being located closely downstream of said injection block and upstream of the control valve.

27. A sampling device according to claim 24 including a flow controller for controlling the carrier gas flow rate in the carrier gas conduit, a solenoid actuated valve in said carrier gas conduit, a timer controlled switch responsive to displacement of said turntable toward said needle to open said valve.

* * * * *

UNITED STATES PATENT AND TRADEMARK OFFICE
CERTIFICATE OF CORRECTION

PATENT NO. : 4,237,733

DATED : December 9, 1980

INVENTOR(S) : Bruno Kolb et al.

It is certified that error appears in the above—identified patent and that said Letters Patent is hereby corrected as shown below:

Column 9, line 15, "posiion" should read -- position --.

Column 9, line 62, change "in" to -- on --.

Signed and Sealed this

Second Day of Jun. 1981

[SEAL]

Attest:

RENE D. TEGTMEYER

Attesting Officer     Acting Commissioner of Patents and Trademarks